United States Patent [19]

Chang

[11] Patent Number: 4,711,843
[45] Date of Patent: Dec. 8, 1987

[54] **METHOD AND VECTOR ORGANISM FOR CONTROLLED ACCUMULATION OF CLONED HETEROLOGOUS GENE PRODUCTS IN *BACILLUS SUBTILIS***

[75] Inventor: Shing Chang, Hercules, Calif.

[73] Assignee: Cetus Corporation, Emeryville, Calif.

[21] Appl. No.: 461,248

[22] Filed: Jan. 26, 1983

Related U.S. Application Data

[63] Continuation of Ser. No. 221,800, Dec. 31, 1980, abandoned, which is a continuation-in-part of Ser. No. 128,537, Mar. 10, 1980, abandoned.

[51] Int. Cl.$^4$ .................... C12P 21/00; C12P 21/02; C12P 21/04; C12P 19/34; C12N 15/00; C12N 9/86; C12N 1/00; C12N 1/20; C12R 1/125; C12R 1/19; C07H 21/04
[52] U.S. Cl. .................................... 435/68; 435/70; 435/71; 435/91; 435/172.1; 435/172.3; 435/231; 435/243; 435/253; 435/317.1; 435/839; 435/849; 536/27; 935/29; 935/41; 935/47; 935/48; 935/52; 935/56; 935/72; 935/73; 935/74
[58] Field of Search .................. 435/68, 70, 91, 172.3, 435/253, 839, 243, 231, 172.1, 849, 71; 935/29, 38, 39, 41, 45, 47, 72, 74, 48, 52, 73; 536/27

[56] References Cited

U.S. PATENT DOCUMENTS

| | | | |
|---|---|---|---|
| 4,237,224 | 12/1980 | Cohen et al. | 435/172 |
| 4,342,832 | 8/1982 | Goeddel et al. | 435/91 |
| 4,411,994 | 10/1983 | Gilbert et al. | 435/172.3 |
| 4,431,740 | 2/1984 | Bell et al. | 435/253 |

FOREIGN PATENT DOCUMENTS 2048894 12/1980 United Kingdom ............. 435/172.3

OTHER PUBLICATIONS

Smith et al., "Extracellular Labeling of Growing Secreted Polypeptide Chains in *Bacillus subtilis* with Diazoiodosulfanilic Acid", *Biochemistry* 18: 198 (1979).
Davies et al., "Plasmid–Determined Resistance to Antimicrobial Agents", *Annual Rev. Microbiol.*, vol. 32, pp. 469, 480, 481, and 482 (1978).
Chang et al., "Expression of Eukaryotic Genes in *B. subtilis* Using Signals of penP", in *Molecular Cloning and Gene Regulation in Bacilli*, Ganesan et al. (ed.), 1982, Academic Press, New York, pp. 159–169.
*Genes*, Lewin, John Wiley & Sons, New York, 1983, p. 673.
Davis et al.: *Nature* 283, 433 (1980).
Taniguchi et al., *Proc. Japan. Acad.* 55, Ser. B, 464 (1979).
Gray and Chang, *J. Bacteriol.*, 145:422–428 (1981).
Hori and Osawa, *PNAs* (USA) 76:381–385 (1979).
Lovett et al., *Methods in Enzymology*, vol. 68:342 (1979).
Rubin et al., *Chem. Abstr.* 93, 14613p (1980).
Gryczan et al., *Molec. Gen. Genet.* 177:459 (1980).
Gryczan et al., *J. Bacteriol.* 141:246 (1980).
Young et al., *Genetic Engineering*, Chakrabarty (ed.) CRC Press, 1978, pp. 145–147.
Keggins et al., *Proc. Natl. Acad. Sci. USA* 75:1423 (1978).
Erlich *Proc. Natl. Acad. Sci. USA* 74:1680 (1977).
Erlich *Proc. Natl. Acad. Sci. USA* 75:1433 (1978).
Gryczan et al., *Proc. Natl. Acad. Sci. USA* 75:1428 (1978).
Duncan et al., *Chem. Abstr.* 86:185728k (1977).
Kreft et al., *Chem. Abstr.* 89:103524r (1978).

*Primary Examiner*—James Martinell
*Attorney, Agent, or Firm*—Elliott L. Fineman; Jane McLaughlin; Virginia Meyer

[57] ABSTRACT

A method and a cloning vector are described for the controlled accumulation of cloned heterologous gene products in *Bacillus subtilis*. The cloning vector is capable of being replicated in *B. subtilis* and includes the heterologous gene located and oriented such as to be under the control of an operator, promoter, and ribosomal binding site sequence. The gene codes for a protein which is under the control of a transport mechanism by which the protein is secreted by the *B. subtilis*. The gene product is recovered from the growth medium for the *B. subtilis*. The cloning vector is also capable of similar use in other bacteria such as *E. coli*.

40 Claims, 6 Drawing Figures

B. LICHENIFORMIS PEN P GENE

BETA LACTAMASE PROMOTER SEQUENCE:

| Sequence | Nucleotides |
|---|---|
| GGTCATCATTTCCTTCCGAAAAACGGTTGCATTTAAATCTTACATATGTAATACTTTCA<br>CCAGTAGTAAAGGAAGGATTTTTTGCCAACGTAAATTTAGAATGTATACATTATGAAAGT | 60 |

<u>Hinf</u>

| AAGACTACATTTGTAAGATTTGATGTTTGAGTCGGCTGAAAGATCGTACGTACCAATTAT<br>TTCTGATGTAAACATTCTAAACTACAAACTCAGCCGACTTTCTAGCATGCATGGTTAATA | 120 |
| TGTTTCGTTGATTGTTCAAGCCATAGTCGGTATTGTGATAATCACCTTTCTCACGAAGTAGACC<br>ACAAAGCAACTAACAAGTTCGGTATTGTGTACATCCCTATCACTGAAAGAGTGCTTCATCTGG | 180 |
| TTACGATCAATCAAATATTCAAGGGGAGACGATTTGATGAAATTATGGTTCAGTA<br>AATGCTAGTTAGTTTATAAGTTTGCCCTCTCTGCTAAAACTACTTTAATACCAAGTCAT | 240 | fMet Lys Leu Trp Phe Ser
5
SIGNAL PEPTIDE

<u>Pst I</u>

| CTTTAAAACTGAAAAAGGCTGCAGTGTTGCTTTTCTCTTGCGTCGCGCTTGCAGGAT<br>GAAATTTTGACTTTTTCCGACGTCGTCACGACGCAGCGCGAACGTCCTA | 300 |

Thr Leu Lys Leu Phe Ser Cys Val Ala Leu Ala Gly
10      15      20      25

| GCGCTAACAATCAAACGAATGCC TCGCAAACCTGCCGAGAATGAAAGACGGAGATGA<br>CGCGATTGTTAGTTTGCTTACGG AGCGTTTGGACGGCTCTTCTTACTTTTCTGCCTCTACT | 360 |

Cys Ala Asn Gln Thr Asn Ala Ser Gln Pro Ala Glu Lys Asn Glu Lys Thr Glu Met
30 SIGNAL PEPTIDE    35 MATURE PROTEIN    40      45

| AAGATGATTTGCAAACGTTAGTTTTGAACTCGTTTAAACTACGTTTTGAGCCCTAGAAACGTAACC<br>TTCTACTAAACGTTTGCAATCAAACTTGATGCAAAAACTCGGGACTGAGCCCTAGAAACGTAACC | 420 |

Lys Asp Phe Ala Lys Leu Glu Leu Glu Gln Phe Asp Ala Lys Leu Gly Ile Phe Ala Leu
50              55              60              65

ATACAGGTACAAACCGG......<br>TATGTCCATGTTTGGCC......

Asp Thr Gly Thr Asn Arg
70

AMINO ACIDS

METHOD AND VECTOR ORGANISM FOR CONTROLLED ACCUMULATION OF CLONED HETEROLOGOUS GENE PRODUCTS IN *BACILLUS SUBTILIS*

This is a continuation of application Ser. No. 221,800, filed Dec. 31, 1980, now abandoned which is a continuation-in-part of application Ser. No. 128,537, filed Mar. 10, 1980, now abandoned.

This invention relates to molecular biology and, more particularly, to the so-called art of recombinant DNA. Specifically, the invention relates to a method and a cloning vector for the controlled accumulation of cloned heterologous gene product in *Bacillus subtilis* and other bacteria, thereby facilitating the recovery of the gene product.

The invention discloses three unique genetically engineered plasmids. Organisms containing these plasmids have been deposited with the American Type Culture Collection, Rockville, Md., 20852. They have been assigned ATCC numbers: 31,776–31,778. ATCC number 31,776 has been assigned to plasmid pOG1196; number 31,777 has been assigned to plasmid pOG2165; and number 31,778 has been assigned to plasmid pOG2110. Applicant has directed that the plasmids be freely available to the general public upon the issuance of a U.S. patent.

As is well known, the particular sequence of amino acids in a given protein is determined in accordance with the code carried in the gene for that protein. In the process of translation by which proteins are formed from DNA, via messenger RNA, groups of three nucleotides in the DNA, called codons, each place one of twenty possible amino acids at a corresponding position in the protein chain.

With the advent of recombinant DNA techniques, genetic changes may be made deliberately by the introduction of a predetermined nucleotide sequence, either synthesized or isolated from one strain or species, into the genetic makeup of another strain or species. The known nucleotide sequence may be selected to cause the strain or species into which it is introduced to produce, as part of the translation process, the protein encoded by the known nucleotide sequence. When the modified strain or species proceeds with the normal replication process, it also then duplicates the inserted sequence.

Recombinant DNA techniques involve isolating a suitable piece of a DNA chain (a cloning vector) and breaking or severing the two strands of DNA of the cloning vector at the desired location where the foreign DNA is to be inserted. To do this, particular types of proteins, called restriction enzymes, are typically used. Restriction enzymes will break the DNA at particular nucleotide sequences, although with some restriction enzymes the break may not necessarily occur at the same point on the two intertwined DNA strands. In such a case, if two different types of DNA are severed in a similar manner, the open ends will be complementary and will, under suitable conditions, stick together with the complementary ends lying side by side. They may then be linked together enzymatically (with ligase). This makes it possible to recombine two DNA segments from any source into a single DNA molecule.

Once the DNA vector has been isolated and the foreign piece inserted therein, the recombinant DNA is then placed into a suitable host organism. In order for the host organism to replicate the inserted DNA, it is necessary that the recombinant DNA be inserted into the host in such a way as to become part of its genetic system.

For example, in the bacterium *Escherichia coli*, two convenient types of cloning vectors have been utilized. *E. coli* bacteria, in addition to the main DNA chain or chromosome, frequently have one or more independently replicating circular loops of DNA known as plasmids. Also, a certain type of virus known as a lambda bacteriophage (phage) is also capable of infecting *E. coli* and becoming part of its genetic system. Recombinant DNA techniques have included the use of a variety of plasmids or phages as cloning vectors. This involves the isolation of plasmids or phages from the bacteria, the breaking open of the isolated DNA by restriction enzymes, the insertion of a foreign or heterologous piece of DNA into the plasmid or phage, the restoration of the circular form of the plasmid or the phage structure, and the return of the plasmid or phage to the *E. coli* cell. Once in the host, the heterologous DNA is not only replicated from generation to generation, but also will produce the protein for which it codes if the proper reading frame and promoters exist.

Once heterologous DNA has been successfully recombined into a host microorganism, and the microorganism has produced the cloned gene product, the desired product must be recovered. To do this it has, up to the present invention, been necessary to destroy the cells producing the desired product in order to harvest the product itself. Also, because cells naturally contain a great many different proteins, the isolation process for the desired product may be difficult or complex. Finally, the desired product may be detrimental to the host cell, particularly if it is produced at a high level. In some cases, this may result in destruction of the cells, and in other cases it may result in the cells activating a defensive mechanism to degrade the desired product.

Most recombinant DNA work to date has been carried out with *E. coli*. *E. coli* is a member of the Gram negative class of bacteria which contain two layers of membranes enclosing a periplasmic space. Many of the products produced in *E. coli* are secreted into this periplasmic space, if secreted at all. Few products are secreted outside the living cells into the growth media.

On the other hand, *Bacillus subtilis* is a member of the gram positive class of bacteria which contain only a single layer of bacterial membrane. Thus *B. subtilis* can produce large amounts of protein which are secreted directly into the growth media. Although the general approach to gene cloning in *E. coli* is applicable to *B. subtilis*, attempts to produce a useful product of heterologous gene cloned into *B. subtilis* and secreted into the growth media have thus far been unsuccessful. *B. subtilis* is somewhat preferable to *E. coli* because of a greater efficiency for plasmid mediated transformation and because it is non-pathogenic.

It is an object of the present invention to provide an improved method for producing heterologous protein by microorganisms.

Another object of the invention is to provide a method for producing a predetermined protein through expression by *B. subtilis*, such protein being non-indigenous to *B. subtilis*.

A further object of the invention is to provide a method for producing protein by *B. subtilis* wherein the protein is non-indigenous to the host species and is secreted into the growth media.

Another object of the invention is to provide a method for producing protein by *E. coli* wherein the protein is non-indigenous to the host species and is secreted into the periplasmic space.

A further object of the invention is to provide a plasmid for producing a predetermined protein through expression by *B. subtilis* or *E. coli*, such protein being non-indigenous to *B. subtilis*.

Other objects of the invention will become apparent to those skilled in the art from the following description, taken in connection with the accompanying drawings wherein:

DETAILED DESCRIPTION OF THE INVENTION

Very generally, and in accordance with one form of the invention, a predetermined protein which is non-indigenous to *B. subtilis* is produced through expression by *B. subtilis*. Growth media and conditions are provided for growing a strain of *B. subtilis* in which a plasmid has been introduced. The plasmid is capable of being replicated in the strain and has a gene therein for the predetermined protein. The gene is located and oriented in the plasmid such as to be under the control of an operator, promoter and ribosomal binding site sequence. The protein is also under the control of a transport mechanism by which the protein is secreted by the host strain. Upon secretion, the protein is recovered from the growth media.

When, according to the invention, the predetermined protein is expressed in a Gram negative bacteria, such as *E. coli*, the protein is again transported across the bacterial membrane by the transport peptide. However, here the protein is "secreted" into the periplasmic space instead of the growth media since the Gram negative bacterium has a cell wall in addition to its normal bacterial membrane. The predetermined protein can be recovered from the periplasmic space.

The method of the invention necessitates the use of a cloning vector organism containing a sequence of nucleotides capable of initiating the transcription and translation process. These nucleotides, which provide an operator, promoter, and ribosomal binding site sequence, may be naturally present in the vector, may be inserted therein as a separate segment of DNA using recombinant DNA techniques, or may be part of the heterologous DNA containing the gene of interest. The heterologous DNA, which will contain at least the structural gene for a desired protein product, is placed in the cloning vector so as to be transcribed and translated under control of the operator, promoter, and ribosomal binding site sequence. For correct translation of the inserted heterologous DNA, the nucleotides in the inserted DNA must be in the correct reading frame. In addition, it may be desirable or even necessary that the cloning vector include a sufficient number of nucleotides indigenous to the host cell to ensure read-through translation from the operator, promoter, and ribosomal binding site sequence into and through the inserted heterologous DNA in the correct reading frame.

In accordance with the invention, the cloning vector utilized includes a sequence of nucleotides which comprise codons for a functional transport signal peptide sequence. Transport signal peptide sequences are typically short leader sequences of amino acids on newly made proteins. Although the mechanism by which the transport signal peptide sequence operates is not entirely understood, it is believed that the transport protein is excreted by the cell and withdraws that protein appended to it from the cytoplasm as the protein is made. Once the transport function has been performed by the transport signal peptide sequence, the transport sequence may be removed by natural processes.

In accordance with the invention, the heterologous DNA can be inserted into the cloning vector at a location which allows the protein for which it encodes to be transported in accordance with the transport signal peptide sequence coded by the signal codons. Thus, the cloned gene product can be conveniently transported to a desired destination from which the gene product may be harvested. This has several advantages. Because the destination is outside the cell, the host cells need not be destroyed to harvest the gene products, thus allowing for the continuous or uninterrupted production of the gene product. Also, since cells contain a great many proteins, the ability to export the cloned gene product makes the isolation and purification of the product a much simpler task. Finally, since cloned gene products, especially if produced at a high level, may be detrimental to the host cells, the ability to harvest the cloned gene products from outside of the cell membranes often means that the products will not harm the cells, nor will the cells possibly produce a defensive enzyme which will degrade the gene product.

The precise location at which the heterologous DNA must be inserted in the cloning vector will, of course, depend upon how the transport signal peptide sequence functions. In some cases, the transport signal peptide sequence will immediately precede the heterologous DNA, either as part of the gene itself or having already been present in the plasmid. The signal sequence itself can constitute the necessary sequence of nucleotides to provide for readthrough translation of the heterologous DNA. On the other hand, there may be some cases in which the transport signal peptide sequence must be located elsewhere than immediately preceding the heterologous DNA. In such cases, it may be necessary to produce the desired peptide sequence with some additional amino-acids at the beginning (coded by the extraneous codons) in order to provide the necessary read-through functions.

The following examples illustrate other specific instances in which the invention may be employed, but are not intended to limit the scope of the invention:

EXAMPLE 1

Figure 4:
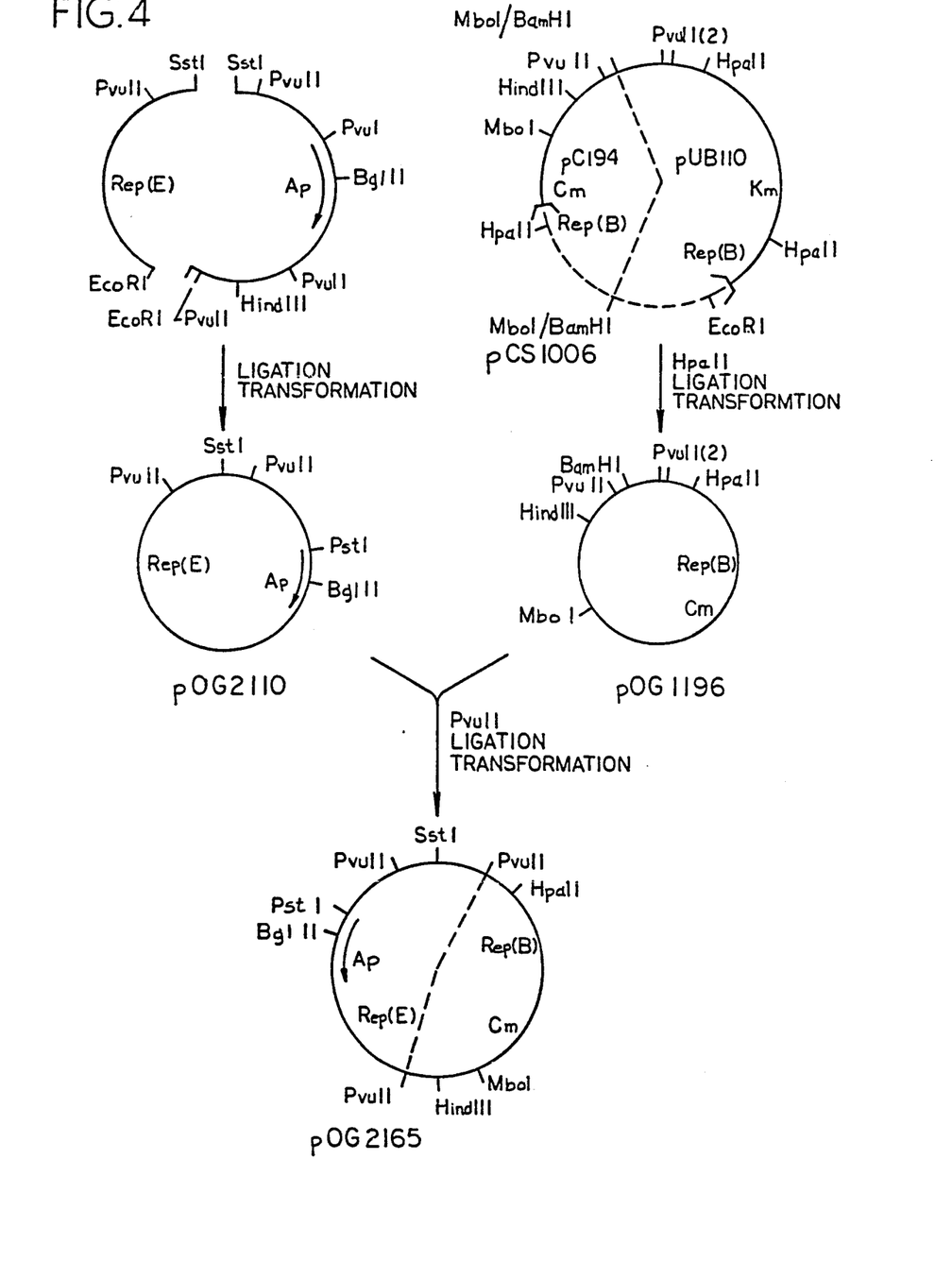
FIG. 4 is a schematic illustration of the construction of *E. coli* plasmid pOG2110, *B. subtilis* plasmid pOG1196, and the bifunctional plasmid pOG2165.

In order to provide a plasmid for producing a predetermined protein non-indigenous to a host organism, a plasmid vector containing the B. licheniformis beta-lactamase gene was made and then replicated in both B. subtilis and E. coli. The plasmid was constructed by purifying a 3.5 kb (kilobase) EcoRI-SstI fragment containing the beta-lactamase gene and then ligating it with a 2.1 kb. EcoRI-SstI fragment containing the replication function of the E. coli plasmid pOP1Δ6 (described by Gelfand, et al., Proc. the Nat. Acad. Sci. USA (1978) 75, 5869–5873). Following transformation into competent E. coli CS412 cells (an $r_k^- m_k^+$ Pro$^-$ derivative of C600) and a growth period adequate for expression (90 minutes), Ap-resistant transformants were obtained. Plasmids from three clones were prepared; one designated as pOG2110 was further characterized. FIG. 4 details the location of the expected and observed restriction sites in pOG2110.

To allow for replication of pOG2110 in B. subtilis, a bifunctional replicon was constructed using pOG2110 and the B. subtilis plasmid pOG1196. The construction of pOG1196 is summarized in FIG. 4.

Initially a chimeric plasmid (pCS832) containing the entire sequences of plasmids pC194 (Cm$^R$) and pUB110 (km$^R$) was made by ligating the two MboI fragments of pC194 with the BamHI digested pUB110. The resulting plasmid carried both the Cm gene from PC194 and the Km (Nm) gene from pUB110. It has a size of 7.5 kb. A spontaneous deletion mutant (plasmid pCS1006) was obtained from one of the sub-clones. It had lost the HpaII site originated in pC194 and known to be located in the pC194 replication region (Chang and Cohen, Molec. Gen. Genet., (1979) 168, 111–115). It still retained the replication function of pUB110 and the two resistance markers. By recirculating the largest HpaII fragment (3.6 kb) of PCS1006, plasmid pOG1196 was obtained. This plasmid confers only Cm-resistance and possesses the replication function derived from plasmid pUB110. The map of pOG1196 is shown in FIG. 4.

E. coli plasmid pOG2110 and B. subtilis plasmid pOG1196 contained two and three PvuII sites respectively. Equal amounts of PvuII digested pOG2110 and pOG1196 plasmid DNA were ligated and used to transform E. coli strain CS412. Cm-resistant clones were selected; all were also Ap-resistant. The composite plasmid pOG2165 isolated from one of the Cm-resistant Ap-resistant transformants was studied further. A map of this 7.5 kb plasmid is shown in FIG. 4. Plasmid pOG2165 replicates in both E. coli and B. subtilis and confers upon either host both Cm- and Ap-resistance.

Figure 5:
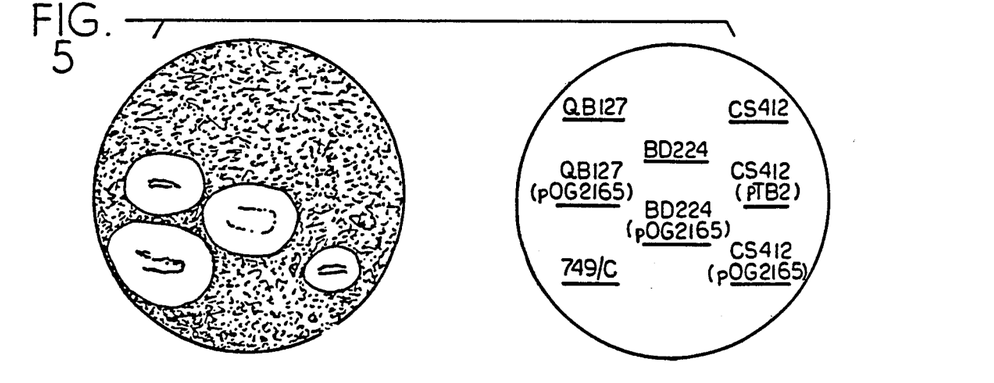
FIG. 5 is a drawing indicating the typical appearance of plates upon which various bacterial strains harboring the recombinant plasmids are grown, as the plates appear after PVA assay for beta-lactamase activity.

B. subtilis and E. coli cells harboring plasmid pOG2165 are resistant to ampicillin as a result of the production of the B. licheniformis beta-lactamase enzyme. This can be demonstrated by means of the PVA plate assay developed by Sherratt and Colling (Ref. 9). The positive results obtained from such an assay are illustrated in FIG. 5.

When pOG2165 is propagated in B. subtilis BD224, both the membrane-bound and the secreted form of the heterologous beta-lactamase are synthesized. The amount produced by this strain is variable and depends upon the growth conditions used. pOG2165 can also be propagated in B. subtilis strain QB127 (Kunst et al, Bio. Chemie. (1974) 56, 1481–1490). QB127 is a bacterial strain with the sacU$^h$ mutation which causes overproduction of several exoenzymes such as levan-sucrase, alpha-amylase and extra-cellular proteases. Levels of beta-lactamase detected in cultures of QB127 (pOG2165) are similar to those levels detected in BD224 (pOG2165) cultures under the same conditions.

The bi-functional plasmid pOG2165 itself possesses unique sites for restriction enzymes SstI, HindIII, PstI and BglII. Insertion of DNA into the BglII and the PstI sites leads to inactivation of the B. licheniformis beta-lactamase gene and provides an easily recognizable phenotype for identifying clones carrying inserts.

When the exact reading frame of the DNA sequence to be inserted is known, it is possible to create a fused protein containing the leader sequence and the first 71 amino acid residues of the beta-lactamase exoenzyme by cloning into the BglII site. Fused protein made in this way is secreted by the Bacillus cells due to the presence of the leader sequence at the amino terminus. These features make pOG2165 a useful vector for the cloning and efficient expression of heterlogous genes, and the subsequent secretion of the gene product in B. subtilis and E. coli.

On the other hand, when the exact reading frame of the DNA sequence to be inserted is known, and insertion is made at the PstI site, a fused protein is made which will accumulate in the host organism. Since the PstI recognition site is located in the initial portion of the nucleotide sequence coding for the signal peptide, only a portion of this sequence is transcribed before the heterologous gene sequence is encountered. Even though the fused protein is expressed, this portion of the signal peptide is insufficient to confer the normal signal peptide's secretion function. As a result, products of genes inserted at the PstI site accumulate in the host organism.

Figure 6:
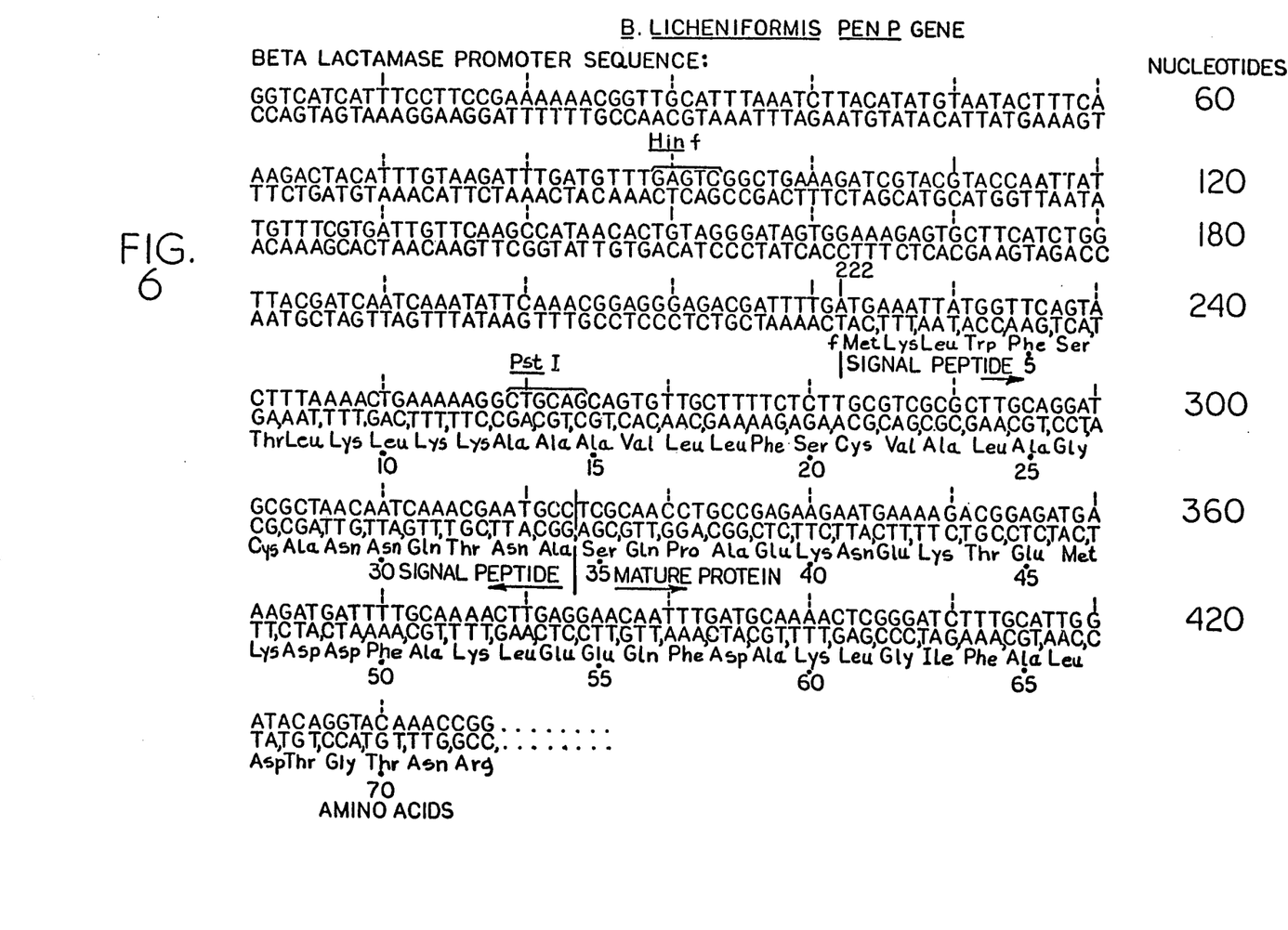
FIG. 6 is a diagram of the nucleotides comprising a portion of the *B. licheniformis* Pen P gene.

A portion of the nucleotide sequence comprising the B. licheniformis Pen P gene is diagrammed in FIG. 6. The beta-lactamase promoter region is located between nucleotides 1 and 221 one; its precise location is unknown. The nucleotides which code for the amino acids comprising the signal peptide begin with nucleotide 222 and end with nucleotide 323. As a result, the signal peptide is composed of thirty-four amino acids. The PstI recognition site is located between nucleotide positions 259 and 264, or at amino acids thirteen through fifteen on the signal peptide chain. Insertion of heterologous DNA into this PstI site will lead to the formation of a fused protein composed of the heterologous DNA product and the first fourteen amino acids of the signal peptide chain. Such a fused protein will be expressed but not transported across the bacterial membrane. Successful secretion requires fusion with either the total signal peptide, or fusion with at least the first twenty six amino acid residues in the signal peptide chain.

EXAMPLE 2

B. licheniformis produces a large amount of beta-lactamase in the secreted form (exo-enzyme). The secretion of this protein is believed to be the result of the interaction between the bacterial membrane and the amino acid leader sequence which facilitates the transport of the protein across the single bacterial membrane barrier. The beta-lactamase gene was cloned and inserted into plasmids which were capable of being replicated in B. subtilis. The plasmids were then transformed into the B. subtilis hosts resulting in the secretion of beta-lactamase. This constitutes the first expression of a heterologous gene in *B. subtilis* and the transport of the gene products into the culture or growth media from the *B. subtilis* cells.

To clone the beta-lactamase gene from the *B. licheniformis* strain, total chromosomal DNA from *B. licheniformis* strain 749/C was isolated and digested with EcoRI restriction endonuclease. Chromosomal DNA isolated from *B. licheniformis* 749/C was prepared according to Marmur (*J. of Molec. Biol.* (1961) 3, 208-18). *E. coli* plasmid pSC101 is isolated from cells using the cleared lysate procedure of Kupersztoch and Helinski (*Biochem. Biophys. Res. Commun.* (1973) 54, 1451-59). 3 µg of chromosomal DNA and 2 µg of pSC101 DNA were digested with endonuclease EcoRI and ligated with T4 DNA ligase as described (Hershfield, et al. *Proc. Natl. Acad. Sci., USA* (1974) 71, 3455-59), and transformed into competent cells of *E. coli* strain CS412 (an $r_k^- m_k^+ Pro^-$ derivative of C600) using the protocol of Cohen, et al. (*Proc. Natl. Acad. Sci., USA* (1972) 69, 2110-14).

Transformants resistant to ampicillin at 10 µg/ml were selected and one of the transformants carrying recombinant plasmid designated pTB2 was characterized further. Plasmid pTB2 carries a 4.2 kb (kilobase pair) EcoRI fragment on the pSC101 vector. This plasmid confers to the host tetracycline (the marker on pSC101) and ampicillin resistances, indicating that the beta-lactamase gene product is made as a functional enzyme which degrades ampicillin in the media.

Figure 1:
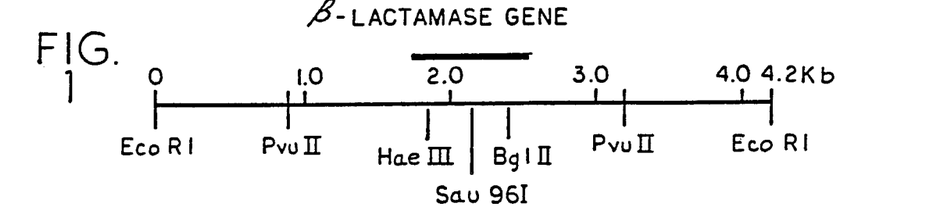
FIG. 1 is a schematic drawing providing a partial structural map of a DNA fragment which contains the gene for beta-lactamase obtained from *Bacillus licheniformis*.

The beta-lactamase gene is located on the 4.2 kilobase pair EcoRI fragment mentioned above. Subsequent analysis of this fragment using various restriction enzymes and gene cloning permits deduction of the structure of the gene for this enzyme is partially mapped and shown in FIG. 1. The primary sequence of the beta-lactamase from *B. licheniformis* strain 749/C has been previously determined (R. J. Meadway, Ph. D., Thesis, University of Edinburgh, 1969). From the known amino acid sequence, the Gly-Pro (position 116-117) sequence corresponds to the nucleotide sequence GGN-CCN, which in turn is the recognition sequence for endonuclease Sau96I (GGNCC). Similarly, the Trp-Pro (position 222-223) sequence is coded by nucleotide codons TGG-CCN, within which the center tetranucleotide sequence GGCC is recognized and cleaved by endonuclease HaeIII (see Roberts, in *DNA Insertion Elements, Plasmids, and Episomes*, 1977, ed. Bukhari, Shapiro and Adhya, Cold Spring Harbor Lab., p. 757).

Figure 2:
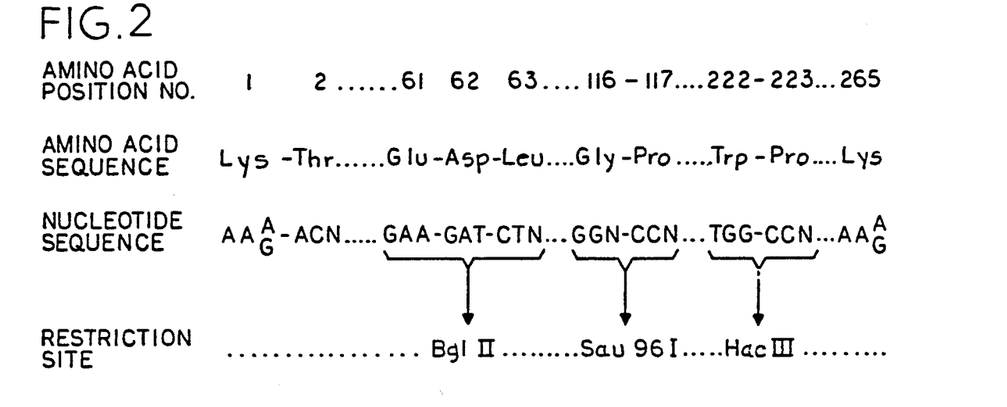
FIG. 2 is a schematic drawing indicating correspondence between a number of the nucleotide sequences in the fragment of FIG. 1 and protein sequence present in the protein for which the fragment codes, and also indicating the corresponding restriction enzyme recognition sites.

The 4.2 kb cloned fragment was analyzed by a number of endonucleases, as listed in FIG. 2, using the conditions specified by the supplier (New England Biolabs, Inc., Beverly, MA 01915, 1978 catalog). The digested DNA was analyzed on agarose gels as described by Sharp, et al. (*Biochemistry* (1973) 12, 3055-63), and on acrylamide gels (Maxam and Gilbert, *Proc. Natl. Acad. Sci., USA* (1973) 73, 3942-46). The mapping data is summarized in FIG. 2. The Sau961 site and the HaeIII site were located in the 2.3 kb PvuII fragment which contains the complete beta-lactamase gene sequence. These two sites are separated by 320 nucleotides which is consistent with the protein sequence data (106 amino acids apart).

Figure 3:
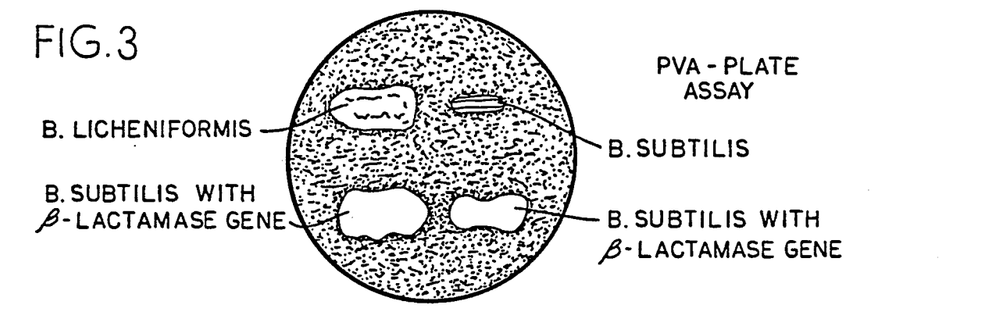
FIG. 3 is a drawing indicating the typical appearance of plates upon which *Bacillus subtilis* strains harboring the recombinant plasmids are grown, as the plates appear after PVA assay for beta-lactamase activity.

After identification of the nucleotide sequence which contains the beta-lactamase gene, the gene was cloned into *B. subtilis* using various Bacillus plasmids and using a hybrid *B. subtilis-E. coli* plasmid. Plasmids included pUB110 and pC221 derived plasmids. The *B. subtilis* strains harboring the recombinant plasmids become resistant to ampicillin as well as give a positive beta-lactamase reaction on PVA plates (see FIG. 3). Furthermore, beta-lactamase activity was detected in cultures after bacterial cells were removed. This activity clearly indicates the successful expression of the heterologous gene in *B. subtilis*, as well as the transport of the protein through the bacterial membrane into the culture or growth media.

The EcoRI fragment containing the beta-lactamase gene was cloned onto *B. subtilis* plasmid vectors pUB110 (Ref. 5) and pC221 (Erlich, *Proc. Natl. Acad. Sci., USA* (1977) 74, 1680-82) at the respective EcoRI sites using the procedure described above in connection with *E. coli*. Similarly, the 2.3 kb PvuII fragment containing the beta-lactamase gene has also been cloned onto pUB110 at the PvuII site and the TacI site.

Ligated DNA preparations were used to transform *B. subtilis* strain BD224 (recE4, trpC2, thr5) by the method of Chang and Cohen (Ref. 7). Transformants resistant to ampicillin on regeneration plates were selected and tested. The production of beta-lactamase is detected by two methods; one is a sensitive plate assay developed by Sherratt and Collins (Ref. 9), the other is the iodometric assay described by Ross and O'Callaghan (*Meth. in Enzymology*, (1975) 43, 69). *B. subtilis* clones resistant to ampicillin gave positive results for both tests. In addition, beta-lactamase activity was also detected in the culture after the cells were removed, indicating that the beta-lactamase is not only made, but also exported in *B. subtilis*.

The cloning of heterologous genes into *B. subtilis* and the functional expression of these genes as intracellular proteins have been shown previously by Keggins et al., Ref. 6. In this study, however, the cloned genes are genes coding for enzymes which are normally present intracellularly in wild type *B. subtilis*. The successful expression of genes which are non-indigenous to *B. subtilis*, and the successful secretion of the products of these genes was not demonstrated.

The work on the beta-lactamase gene presented in this Example is the first demonstration that a new function namely, beta-lactamase production, can be introduced into *B. subtilis* using gene cloning techniques. In addition, this Example constitutes the first demonstration that a foreign gene product can be made to pass through the *B. subtilis* membrane barrier and be secreted as an exo-protein. The beta-lactamase, which is a commercially useful product, is produced by a strain which does not otherwise produce this enzyme.

EXAMPLE 3

The *B. licheniformis* beta-lactamase gene described in Example 2 was also inserted into plasmids capable of being replicated in *E. coli*. These plasmids were transformed into the *E. coli* hosts using methods identical to those described in Example 2 for *B. subtilis*. The *E. coli* cells harboring the plasmids are resistant to ampicillin as a result of the production of the *B. licheniformis* beta-lactamase enzyme. This is demonstrated by means of the PVA plate assay developed by Sherratt and Collins (Ref. 9).

When the *B. licheniformis* beta-lactamase gene carrying plasmids are propagated in *E. coli*, the secreted form of the enzyme is not transported into the culture medium as it is in *B. subtilis*. Since *E. coli* has a cell wall surrounding the limiting bacterial membrane, the heterologous protein product is transported to the periplasmic space separating the cell wall from the bacterial membrane. The beta-lactamase exoenzyme was allowed to accummulate in the periplasmic space and was then harvested by appropriate methods.

EXAMPLE 4

The beta-lactamase gene of *B. licheniformis* is not the only source of a signal peptide sequence that can function in *B. subtilis* or *E. coli*. As indicated above, many proteins (especially in eucaryotic cells) are transported across membranes. Although the precise amino acid sequence of the "signal region" may, and in fact does, vary among different transported proteins, the folded structures of these regions, which can be predicted according to the rules of Chou and Fasman (*Ann. Rev. Biochem.* (1978) 47, 251), are very similar. Thus, the requirements for a transport signal peptide sequence can be satisfied with non-Bacillus signal peptides, provided the signal sequence encoding DNA fragment is correctly positioned downstream from a Bacillus promoter, and ribosomal binding site sequence.

One such eucaryotic transport signal sequence that may be used in connection with a desired gene product is the signal or presequence preceding the insulin B chain. ( The various insulin chains, A, B and C, are made as a single polypeptide and are assembled and processed in the endoplasmic reticulum on the way to being exported by the cell). However, in the insulin presequence there is no convenient restriction site immediately after the signal peptide sequence which can be used to join it with a cloned gene of heterologous DNA. Nevertheless, the last five nucleotides of the signal sequence in insulin are AGGCT and the first nucleotide of the insulin B chain itself is T. These six nucleotides together (AGGCTT) differ by a single nucleotide from AAGCTT which is the recognition sequence for the restriction enzyme HindIII. The enzyme cuts between the two As. If the heterologous DNA was cloned or separated using the same enzyme, HindIII, or using a half HindIII site bifunctional linker, the sequence will be restored when the heterologous DNA is inserted.

The single nucleotide $G_x$ may be changed to an A to provide the HindIII site by the procedure described by Bahl in U.S. patent application Ser. No. 128,671 or by the procedure described by Bahl in U.S. patent application Ser. No. 133,150, U.S. Pat. No. 4,351,901, issued Sept. 28, 1982. In the first case, a small single stranded fragment incorporating the change is synthesized by the method of Narang et al. (*Canadian Journ. of Chem.* 51:3649). In the second procedure, the nucleotide to be changed is exposed, altered, and the sequence reconstructed. In either case, this change results in no alteration of the next to last amino acid of the signal sequence.

DNA ligation may be accomplished as described by Hershfield et al. (*Proc. Natl. Acad. Sci. USA* 71:3455). Reverse transcriptase may be used as a DNA polymerase such as described by Bahl et al. (*Proc. Natl. Acad. Sci. USA* 74:966). Transformation may proceed as described by Cohen et al. (*Proc. Natl. Acad. Sci. USA* 70:3240).

EXAMPLE 5

Although the procedure described in Example 4 above is technically feasible, it is a eukaryotic leader sequence and thus the procedure may be useful only in connection with general research. Typically, a more useful approach from a commercial standpoint is in connection with a prokaryotic (bacterial) host. Although only a few such signal sequences are known in connection with prokaryotic systems, one sequence which is well characterized is the sequence from TEM beta-lactamase. (Sutcliffe *Proc. Natl. Acad. Sci. USA* 75:3737). This sequence is ideal for attaching to a cloned gene except that there is no convenient restriction site at the location for presequence processing. The nearest restriction site to the signal sequence is an MboI site which would result in the attachment of 16 extraneous amino acids to the cloned gene product.

Nevertheless, the terminal portion of the signal sequence, which is TTTGCT, may be altered, by one of the above-described techniques, to TTTGAT. When the latter sequence is read along with the first few following nucleotides of the TEM beta-lactamase gene, a restriction site for BclI (TGATCA) exists. This results in the altering of the final amino acid from Ala to Asp and in the attaching of one extra amino acid to the gene product, either a Glu or His, depending upon what the first attached nucleotide of the heterologous DNA is.

To accomplish the foregoing alteration in nucleotides, the approach described above may be used wherein a short fragment is synthesized. There are bracketing restriction sites upstream from the signal sequence (ThaI) and a restriction site MboI, as mentioned above, downstream. A Taq site exists even further downstream. Restriction conditions may be followed for ThaI as described by McConnell et al., *Nucleic Acid Res.* 5:1729; for MboI by Galinas et al., *J. Mol. Biol.* 114:169; or TaqI by Sato et al., *Proc. Natl. Acad. Sci. USA* 74:542. Note that in connection with MboI, the DNA is prepared in the host cell GM119 which lacks deoxyadenosine methylase (to avoid methylation of regions and prevent MboI cutting). In this latter connection see Marinus et al., *Mutat. Res.* 28:15. Alternatively, the restriction endonuclease SAU 3A, an isoschizome of MboI, may be used with DNA isolated from any host.

It may be seen, therefore, that the invention provides a method and a vector for the controlled accumulation of heterologous cloned gene products. The products are transferred or transported outside the host cell, enabling the harvesting of the product to proceed with minimal restrictions, and avoiding the likelihood of degradation or destruction of either the host cell or the gene product itself.

Various modifications of the invention in addition to those shown and described herein will become apparent to those skilled in the art from the foregoing description and accompanying drawings. Such modifications are intended to fall within the scope of the appended claims.

REFERENCES

1. Cohen, S. N., Chang. A. C. Y., Boyer, H. W., and Helling, R. B., (1973) *Proc. Natl. Acad. Sci. USA* 70, 3240–4.
2. Collins, J., (1977) *Curr. Top. Microbiol. Immunol.* 78, 121–170.
3. O'Farrell, P. H., Polisky, B., and Gelfand, D. H., (1978) *J. Bacteriol.* 134, 645–654.
4. Polisky, B., Bishop, R. J., Gelfand, D. H., (1976) *Proc. Natl. Acad. Sci. USA* 73, 3900–3904.
5. Gryczan, T. J., and Dubnau, D., (1978) *Proc. Natl. Acad. Sci., USA* 75, 1428–1432.
6. Keggins, K. H., Lovett, P. S., and Duvall, E. J., (1978) ibid 1423–1427.

7. Chang, S., and Cohen, S. N., (1979) *Molec. Gen. Genet.* 168, 111–115.
8. Chang, A. C. Y., and Cohen, S. N., (1974) *Proc. Natl. Acad. Sci. USA* 71, 1030–1034.
9. Sherratt, D. J., and Collins, J. F., (1973) *J. Gen. Microbiol.* 76, 217–230.

What is claimed is:

1. A method for producing a predetermined protein comprising providing growth conditions in a growth medium for Gram-positive bacteria containing hybrid cloning vectors, said vectors having a gene therein for said predetermined protein, said predetermined protein being non-indigenous to the Gram-positive bacteria, said gene being located and oriented in said vector such as to be under the control of an operator, promoter, and ribosomal binding site sequence, said predetermined protein being under the control of a transport mechanism comprising a portion of a Bacillus secretion leader sequence that functions for secretion by which said predetermined protein is secreted by said Gram-positive bacteria, culturing said bacteria under conditions suitable for the production and secretion of said predetermined protein, and recovering said predetermined protein from said growth medium.

2. A method according to claim 1 wherein said bacteria are *Bacillus subtilis*.

3. A method according to claim 1 wherein said gene for said predetermined protein is under the control of the beta-lactamase operator, promoter, and ribosomal binding site sequence.

4. A method according to claim 1 wherein said predetermined protein is beta-lactamase.

5. A method according to claim 1 wherein said predetermined protein is a mammalian protein.

6. A method according to claim 1 wherein said predetermined protein is a mammalian hormone.

7. A method according to claim 1 wherein said transport mechanism is provided for by a portion of the *Bacillus licheniformis* β-lactamase secretion leader that functions for secretion.

8. A method according to claim 1 wherein said transport mechanism provided for by a functional portion of a Bacillus secretion leader sequence is a portion of the α-amylase gene.

9. A method for producing a predetermined protein non-indigenous to *Bacillus subtilis* comprising providing growth conditions in a growth medium for *Bacillus subtilis* bacteria containing hybrid cloning vectors, said vectors having a gene therein for said predetermined protein, said gene being located and oriented in said vector such as to be under the control of an operator, promoter, ribosomal binding site sequence, and a transport mechanism comprising a portion of a Bacillus secretion leader sequence that functions for secretion culturing said *Bacillus subtilis* under conditions suitable for the production and secretion of said predetermined protein, and recovering said predetermined protein as a secreted product of said *Bacillus subtilis* bacteria.

10. A method according to claim 9 wherein said transport mechanism provided for by a functional portion of the Bacillus secretion leader sequence is a portion of the α-amylasegene.

11. A method according to claim 9 wherein said gene for said predetermined protein is under the control of the beta-lactamase operator, promoter, and ribosomal binding site sequence.

12. A method according to claim 9 wherein said predetermined protein is beta-lactamase.

13. A method according to claim 9 wherein said predetermined protein is a mammalian hormone.

14. A method according to claim 9 wherein said transport mechanism is provided by a portion of the *Bacillus licheniformis* β-lactamase secretion leader that functions for secretion.

15. A method according to claim 9 wherein said predetermined protein is a mammalian protein.

16. A hybrid cloning vector for producing a predetermined protein through expression of *B. subtilis*, comprising a vector which is capable of autonomous replication in *B. subtilis* and having a gene therein for said predetermined protein, said gene being located and oriented in said vector such as to be under the control of an operator, promoter, and ribosomal binding site sequence, said predetermined protein being under the control of a transport mechanism comprising a portion of a Bacillus secretion leader sequence that functions for secretion by which said predetermined protein is secreted by *B. subtilis*.

17. A hybrid cloning vector according to claim 16 wherein said predetermined protein is a mammalian protein.

18. A hybrid cloning vector according to claim 16 comprising a plasmid selected from the group consisting of: pC221, pUB110, pC194, pUB112, pT127, pOG2165, pOG2110, pOG1196 and pCS832.

19. A hybrid cloning vector according to claim 16 wherein said gene for said predetermined protein is under the control of the beta-lactamase operator, promoter, and ribosomal binding site sequence.

20. A hybrid cloning vector according to claim 16 wherein said predetermined protein is beta-lactamase.

21. A hybrid cloning vector according to claim 16 wherein said predetermined protein is a mammalian hormone.

22. A cloning vector according to claim 16 wherein said transport mechanism is provided for by a portion of the *Bacillus licheniformis* β-lactamase secretion leader that functions for secretion.

23. A cloning vector according to claim 16 wherein said transport mechanism provided for by a functional portion of a Bacillus secretion leader sequence is a portion of the α-amylase gene.

24. A hybrid cloning vector comprising a plasmid selected from the group consisting of pOG2110, pOG1196 and pOG2165.

25. A method for creating a microorganism capable of producing a predetermined protein through expression, comprising, forming a hybrid cloning vector capable of autonomous replication in *B. subtilis* and having a gene therein for said predetermined protein, said predetermined protein being non-indigenous to *B. subtilis*, said gene being located and oriented in said vector such as to be under the control of an operator, promoter and ribosomal binding site sequence, said predetermined protein being under the control of a transport mechanism comprising a portion of a Bacillus secretion leader sequence that functions for secretion by which said predetermined protein is secreted by *B. subtilis* and introducing said vector to *B. subtilis*.

26. A method according to claim 25 wherein said transport mechanism provided for by a functional portion of a Bacillus secretion leader sequence is a portion of the α-amylase gene.

27. A method according to claim 25 wherein said transport mechanism is provided for by a portion of the

*Bacillus licheniformis* β-lactamase secretion leader that functions for secretion.

28. A method according to claim 25 wherein said gene for said predetermined protein is under the control of the beta-lactamase operator, promoter, and ribosomal binding site sequence.

29. A method according to claim 25 wherein said protein is beta-lactamase.

30. A microorganism capable of producing a predetermined protein through expression, comprising a host microorganism, a hybrid cloning vector capable of autonomous replication in said host; said vector having a gene therein for said predetermined protein; said gene being for a predetermined protein which is non-indigenous to said host microorganism; said gene being located and oriented in said vector such as to be under the control of an operator, promoter and ribosomal binding site sequence, said predetermined protein being under the control of a transport mechanism comprising a portion of a Bacillus secretion leader sequence that functions for secretion by which said predetermined protein is secreted by said host microorganism.

31. A transformant bacterial culture cloned from a microorganism according to claim 30, the members of said culture being capable of expressing said predetermined protein.

32. A microorganism according to claim 30 wherein said transport mechanism provided for by a functional protein of a Bacillus secretion leader sequence is a portion of the α-amylase gene.

33. A microorganism according to claim 30 wherein said host microorganism is selected from the group consisting of *B. subtilis* and *E. coli*.

34. A microorganism according to claim 30 wherein said hybrid cloning vector comprises a plasmid selected from the group consisting of pC221, pUB110, pC194, pUB112, pT127, pOG2165, pOG2110, pCS1006, pOG1196, pCS832.

35. A microorganism according to claim 30 wherein said gene or said predetermined protein is under the control of the beta-lactamase operator, promoter, and ribosomal binding site sequence.

36. A microorganism according to claim 30 wherein said predetermined protein is a mammalian protein.

37. A microorganism according to claim 30 wherein said predetermined protein is a mammalian hormone.

38. A microorganism according to claim 30 wherein said predetermined protein is beta-lactamase.

39. A microorganism according to claim 30 wherein said hybrid vector is a bifunctional plasmid vector having unique sites for restriction enzymes SstI, HindIII, PstI, and BglII.

40. A microorganism according to claim 30 wherein said transport mechanism is provided for by a portion of the *Bacillus licheniformis* β-lactamase secretion leader that functions for secretion.

* * * * *